United States Patent [19]
Cormier et al.

[11] Patent Number: 5,902,779
[45] Date of Patent: May 11, 1999

[54] SHOWER AND SHAVE BODY WASH

[75] Inventors: Pam A. Cormier; Laura A. Schick, both of Newburgh, N.Y.; Mary L. Posten, Ridgewood, N.J.

[73] Assignee: Avon Products, Inc., New York, N.Y.

[21] Appl. No.: 08/949,218

[22] Filed: Oct. 10, 1997

[51] Int. Cl.$^6$ ............... C11D 3/30; C11D 1/62; C11D 17/08; C11D 10/00
[52] U.S. Cl. ............ 510/159; 510/405; 510/483; 510/488; 510/504
[58] Field of Search ............... 510/504, 482, 510/488, 159, 405

[56] References Cited

U.S. PATENT DOCUMENTS

| | | |
|---|---|---|
| 2,435,829 | 2/1948 | Guest . |
| 2,589,674 | 3/1952 | Cook et al. . |
| 4,275,055 | 6/1981 | Nachtigal et al. ............ 424/70 |
| 4,278,570 | 7/1981 | Flom . |
| 4,310,433 | 1/1982 | Stiros . |
| 4,450,091 | 5/1984 | Schmolka . |
| 4,673,525 | 6/1987 | Small et al. . |
| 4,753,747 | 6/1988 | Clark et al. . |
| 4,765,922 | 8/1988 | Contamin et al. . |
| 4,812,253 | 3/1989 | Small et al. . |
| 4,950,468 | 8/1990 | Nakamura et al. . |
| 4,954,335 | 9/1990 | Janchipraponvej . |
| 4,954,538 | 9/1990 | Dauplaise et al. . |
| 4,976,953 | 12/1990 | Orr et al. . |
| 4,978,526 | 12/1990 | Gesslein et al. . |
| 4,994,088 | 2/1991 | Ando et al. . |
| 5,057,497 | 10/1991 | Calam et al. . |
| 5,059,414 | 10/1991 | Dallal et al. . |
| 5,076,953 | 12/1991 | Jordan et al. . |
| 5,096,608 | 3/1992 | Small et al. . |
| 5,124,313 | 6/1992 | Schaeffer et al. . |
| 5,149,522 | 9/1992 | Schwarz et al. . |
| 5,208,013 | 5/1993 | Klein . |
| 5,215,759 | 6/1993 | Mausner . |
| 5,256,649 | 10/1993 | Le Fur et al. . |
| 5,288,484 | 2/1994 | Tashjian . |
| 5,306,706 | 4/1994 | Baydar et al. ............... 512/2 |
| 5,308,526 | 5/1994 | Dias et al. . |
| 5,312,559 | 5/1994 | Kacher et al. . |
| 5,328,685 | 7/1994 | Janchitraponvej et al. . |
| 5,340,571 | 8/1994 | Grace . |
| 5,340,865 | 8/1994 | Neff et al. . |
| 5,378,731 | 1/1995 | Andrews et al. . |
| 5,384,118 | 1/1995 | La Valle . |
| 5,415,861 | 5/1995 | Duffy et al. . |
| 5,417,876 | 5/1995 | Tokosh et al. . |
| 5,441,671 | 8/1995 | Cheney et al. . |
| 5,496,538 | 3/1996 | Zimmerman et al. . |
| 5,529,714 | 6/1996 | Tokosh . |
| 5,534,265 | 7/1996 | Fowler et al. . |
| 5,556,615 | 9/1996 | Janchitraponvej et al. . |
| 5,587,154 | 12/1996 | Dowell et al. . |
| 5,635,469 | 6/1997 | Fowler et al. . |
| 5,714,270 | 2/1998 | Malhotra et al. ............ 428/537.5 |
| 5,733,535 | 3/1998 | Hollingshead et al. ............ 424/65 |

OTHER PUBLICATIONS

Inolex: L'attualita nella Tradizione/Inolex: Then and Now, Cosmetic News, No. XIV–81 (1991), pp. 415–421—original and translation.

McCutcheon's, Vol. 2: Functional Materials, Conditioners/Hair & Skin, p. 64, 1996 North American Edition.

*Manufacturing Chemist*, "Soothing Away Shaving Discomfort", Dec. 1988, pp. 41, 43, 44.

*Manufacturing Chemist*, "Formulating for a Close Shave", Nov. 1988, pp. 67–68.

*Manufacturing Chemist*, "Formulating for a Close Shave", Oct. 1988, pp. 53, 55, 56, 59.

*Primary Examiner*—Paul Lieberman
*Assistant Examiner*—John M. Petruncio
*Attorney, Agent, or Firm*—Ohlandt, Greeley, Ruggiero & Perle, L.L.P.

[57] ABSTRACT

A substantially transparent liquid cleanser includes water, a fatty acid surfactant, and from about 0.1 weight percent to about 6 weight percent behenamidopropyl PG-dimonium chloride. This cleanser provides a luxurious lather that cleanses, conditions, and can function as a shaving foam.

23 Claims, No Drawings

SHOWER AND SHAVE BODY WASH

The present invention relates generally to a composition that is useful as a body wash. More particularly, this invention relates to a composition that, on contact with water, provides a substantial and long-lasting lather that is suitable as a body wash and a shaving foam. The resulting composition is preferably clear or translucent, and provides an enhanced satiny or silky feel on the skin.

BACKGROUND OF THE INVENTION

Body washes are growing in popularity as personal cleansers. These body washes are liquid cleansing compositions that can be used in the shower or bath instead of soap bar products. A body wash liquid can be applied directly to the skin, or can be applied to a washcloth, sponge or other carrier. Typically, these body wash cleansers provide a very weak and short-lived lather. Many consumers find such products inadequate, and that such cleansers do not leave their skin feeling sufficiently clean. Accordingly, a demand exists for a body wash that has a thick and long-lasting lather.

In addition, body cleansers with a fatty acid backbone do not typically appear clear due to their intrinsic chemistry. However, transparent products provide a unique appearance that is preferred by many consumers, since they can appear cleaner, more pure, and aesthetically more interesting than opaque cleansers Heretofore, a need has existed for a transparent body wash. The transparency of the cleansers of the present invention is due to their unique blend of fatty acids and neutralization.

The present inventors developed and marketed over a year ago a unique transparent body wash that is suitable as a cleanser and shaving foam. This body wash included: water, glycerin, sodium chloride (a viscosity increasing agent), tetrasodium EDTA, propylene glycol, polyethylene glycol 300-NF, fatty acids, potassium hydroxide (a pH adjuster), sodium lauroamphoacetate, glycol distearate, preservatives, color and fragrance.

It has now surprisingly been discovered that body wash compositions of that type can be improved aesthetically by the addition of a behenamidopropyl PG-dimonium chloride/PG/AQ, which acts as a skin conditioner and viscosity increasing agent. The resulting body wash has a superior feel and texture before and after lathering. The lather produced is a luxurious foam. Moreover, skin is left in an improved state—softer and less dry—after cleansing.

SUMMARY OF THE INVENTION

Against the foregoing background, it is a primary object of the present invention to provide a substantially transparent body wash composition.

It is another object of the present invention to provide such a body wash composition that is a cleanser.

It is a further object of the present invention to provide a cleanser that provides a silky and smooth feel when applied to the body, and that generates a substantive and long-lasting lather or foam.

It is a still further object of the present invention to provide such a cleanser that can also be used as an effective body shaving lubricant.

To the accomplishment of the foregoing objects and advantages, the present invention, in brief summary, is a cleanser that includes water, a fatty acid surfactant, and from about 0.1 weight percent to about 6 weight percent behenamidopropyl PG-dimonium chloride.

DESCRIPTION OF THE PREFERRED EMBODIMENTS

The present invention provides unique cosmetic liquid cleansers or cleansing compositions that are substantially transparent and that have a smooth, silky feel on contact with the skin. Moreover, the liquid cleansing compositions of the present invention provide a vigorous and durable foamy lather that has dual functions. The foamy lather cleanses and conditions the skin, and simultaneously acts as a shaving foam or lubricant. This eliminates the need for separate cleansing and shaving compositions. Moreover, the rich creamy lather provides a comfortable shave and does not clog razors, but instead rinses away easily.

The cleansing compositions according to the present invention preferably include a solvent and surfactants/cleansing agents in combination with a skin conditioner and viscosity increasing agent—behenamidopropyl PG-dimonium chloride, with a structural formula as follows:

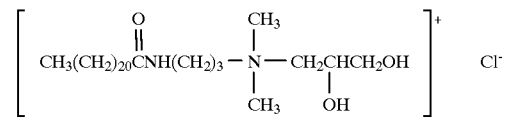

This behenamidopropyl PG-dimonium chloride is preferably used in a commercially available propylene glycol and water base, namely as behenamidopropyl PG-dimonium chloride/PG/AQ.

The solvent is preferably water, and more preferably demineralized water. The amount of water in the preferred cleansing compositions is about 45 percent to about 55 percent by weight of the total weight of the composition.

The surfactants/cleansing agents act to lift dirt and oils away from the skin surface, so they can easily be rinsed away. The preferred surfactants/cleansing agents are fatty acids. While many fatty acids will function in the present invention, the preferred fatty acids are the C-10 to C-20 fatty acids, or mixtures of two or more thereof. More preferred is a mixture of lauric acid, myristic acid, palmitic acid and stearic acid. These surfactants are preferably present at about 5 to about 10 weight percent, more preferably at about 7.5 to about 8.5 weight percent.

Surfactants, preferably amphoteric surfactants, and more preferably sodium lauroamphoacetate, can also be used in combination with the fatty acids, to achieve the desired level of cleansing action. These surfactants can be used as secondary or tertiary surfactants in the cleansers of the present invention.

In the present invention, the behenamidopropyl PG-dimonium chloride/PG/AQ acts as a skin conditioner, a viscosity increasing agent and a solubilizer. The addition of this component to the cleansers surprisingly provides a superior consistency and feel to the product, both as it is dispensed and when it is lathered. It additionally allows a range of composition viscosities to be achieved, improves solubility, improves stability over freeze/thaw cycles, permits the addition of fragrance with no negative effect on the base, and gives a silkier, smoother feel to the lather and to the cleansed skin. This component is preferably present at about 0.1 to about 6 weight percent, more preferably at about 4 weight percent.

The cleansing compositions of the present invention may include one or more combined supplemental skin conditioners and viscosity increasing agents. Preferred combined supplemental skin conditioners and viscosity increasing agents include sodium isostearoyl lactylate and lauryl lactylate. Preferred total levels of such ingredients are about 0.1 to about 6 weight percent. Most preferably, about 2.5 weight percent is used.

The preferred cleansing compositions may also include skin conditioners and humectants, in addition to the behenamidopropyl PG-dimonium chloride, to leave the skin softer, smoother, and less dry. The preferred skin conditioners and humectants for use include glycerin, glycol distearate (also an opacifying agent), propylene glycol (which also functions as a cold temperature stabilizer), polyethylene glycol 300-NF (which also functions as a viscosity decreasing agent), and mixtures of the foregoing. Sodium lauroamphoacetate can also be used for its skin conditioning properties, in addition to its surfactant and foam boosting properties. Such skin conditioners and humectants are preferably present at about 10 to about 25 weight percent, more preferably at about 15 to about 20 weight percent.

In addition, a pH adjuster is preferably used to keep the pH of the cleansers at about 8.5 to about 9.5, and ideally about 8.8 to about 9.2. The preferred pH adjuster for use in the cleansing compositions of the present invention is potassium hydroxide, which is commercially available as a 45% pure product. The pH adjuster is preferably present at about 9 weight percent to about 13 weight percent, more preferably at about 10.5 weight percent to about 11.5 weight percent.

A chelating agent may also be added to the cleansing compositions of the present invention to help retard oxidation. Preferably, tetrasodium EDTA is used as the chelating agent in these cleansing compositions. The chelating agent is preferably present at about 0.01 weight percent to about 0.2 weight percent, more preferably at about 0.025 to about 0.1 weight percent.

In addition, the viscosity of the finished cleansing compositions can be further modified by the use of other viscosity increasing agents and viscosity decreasing agents. A most preferred viscosity increasing agent for use in the cleansing compositions of the present invention is sodium chloride. Magnesium chloride and potassium chloride are also preferred. The viscosity increasing agents are preferably present at about 1.5 weight percent to about 6 weight percent, more preferably at about 4 weight percent to about 5 weight percent. Viscosity decreasing agents may also be used. A preferred component that would act as a viscosity decreasing agent is polyethylene glycol 300-NF, which is preferably present at up to about 0.5 weight percent, more preferably at about 0.1 weight percent to about 0.3 weight percent.

Other ingredients, such as colorants, fragrances, UV stabilizers, preservatives and aqueous extracts of vitamins and other active ingredients, can be added to the cleansing compositions of the present invention. These ingredients can be added at up to about 1 weight percent, more preferably up to about 0.4 weight percent. A particularly preferred preservative for use in the cleansing compositions of the present invention is imidazolidinyl urea.

The substantially transparent nature of the compositions of the present invention provides unique aesthetics that are appealing to the consumer. It is believed that the transparency of the cleansing compositions is achieved due to the proper balance of fatty acids and neutralization, as set forth above. However, the simple addition of opacifying agents, as known in the art, such as glycol distearate, ethylene glycol monostearate and guanine, can convert the cleansers or cleansing compositions to translucent or opaque liquids, to give them pearlescent, creamy or other appearances.

Accordingly, preferred cleansers according to the present invention may include the following:

|  | Preferred Range in weight percent |
|---|---|
| Glycerin | 2.00–8.00 |
| Sodium chloride | 1.50–6.00 |
| Tetrasodium EDTA | 0.025–0.10 |
| Potassium hydroxide 45% | 10.50–11.50 |
| C-10 to C-20 fatty acids | 19.00–25.00 |
| Sodium lauroamphoacetate | 7.50–8.50 |
| Glycol distearate | 0.00–2.00 |
| Fragrance | 0.00–2.00 |
| Propylene glycol | 1.25–2.50 |
| Imidazolidinyl urea | 0.00–0.40 |
| Polyethylene glycol 300-NF | 0.00–0.30 |
| Behenamidopropyl PG-dimonium chloride/PG/AQ | 0.10–6.00 |
| Sodium isostearoyl lactylate | 0.00–5.00 |
| Aqueous Extracts | 0.00–1.00 |
| UV stabilizers | 0.00–0.20 |
| Colorants | 0.00–0.50 |
| Water | 45.00–55.00 |

The present invention having been thus described with particular reference to the preferred forms thereof, it will be obvious that various changes and modifications may be made therein without departing from the spirit and scope of the invention as defined in the appended claims.

What we claim is:

1. A substantially transparent cleanser comprising:
   solvent;
   a fatty acid surfactant; and
   from about 0.1 weight percent to about 6 weight percent behenamidopropyl PG-dimonium chloride.

2. The cleanser of claim 1, wherein said solvent includes water.

3. The cleanser of claim 1, further comprising a skin conditioner selected from the group consisting of glycerin, glycol distearate, propylene glycol, polyethylene glycol 300, sodium isostearoyl lactylate, lauryl lactylate and mixtures thereof.

4. The cleanser of claim 1, further comprising an amphoteric surfactant.

5. The cleanser of claim 4, wherein said amphoteric surfactant is sodium lauroamphoacetate.

6. The cleanser of claim 1, wherein said fatty acid surfactant is a mixture of at least two C-10 to C-20 fatty acids.

7. The cleanser of claim 1, wherein said fatty acid surfactant is present at about 19 to about 25 weight percent.

8. The cleanser of claim 2, wherein said water is present at about 45 to about 55 weight percent.

9. The cleanser of claim 1, wherein said behenamidopropyl PG-dimonium chloride is present at about 4 weight percent.

10. The cleanser of claim 1, further comprising a pH adjuster.

11. The cleanser of claim 10, wherein said pH adjuster is potassium hydroxide.

12. The cleanser of claim 11, wherein said potassium hydroxide is about 45% pure and is present at about 10.5 to about 11.5 weight percent.

13. The cleanser of claim 11, wherein said potassium hydroxide is present at an effective level of about 4.5 to about 5.5 weight percent.

14. The cleanser of claim 1, further comprising a viscosity increasing agent.

15. The cleanser of claim 14, wherein said viscosity increasing agent is sodium chloride.

16. The cleanser of claim 15, wherein said sodium chloride is present at about 1.5 to about 6 weight percent.

17. The cleanser of claim 1, wherein said cleanser has a pH of about 8.5 to about 9.5.

18. The cleanser of claim 1, wherein said cleanser is a shower and shave body wash.

19. The cleanser of claim 1, further comprising a chelating agent.

20. The cleanser of claim 19, wherein said chelating agent is tetrasodium EDTA.

21. A substantially transparent cleanser, comprising:

about 1.5 to about 6 weight percent sodium chloride;

about 0.025 to about 0.10 weight percent tetrasodium EDTA;

about 10.5 to about 11.5 weight percent potassium hydroxide;

about 19 to about 25 weight percent fatty acids;

about 7.5 to about 8.5 weight percent sodium lauroamphoacetate;

about 0.1 to about 6 weight percent behenamidopropyl PG-dimonium chloride; and about 45 to about 55 weight percent water.

22. The cleanser of claim 21, further comprising a skin conditioner selected from the group consisting of glycerin, glycol distearate, propylene glycol, polyethylene glycol 300, sodium isostearoyl lactylate, lauryl lactylate and mixtures thereof.

23. A substantially transparent cleanser comprising:

from about 45 weight percent to about 55 weight percent water;

from about 5 weight percent to about 10 weight percent C-10 to C-20 fatty acids; and from about 0.1 weight percent to about 6 weight percent behenamidopropyl PG-dimonium chloride.

* * * * *